United States Patent
Guan et al.

(10) Patent No.: US 9,828,623 B2
(45) Date of Patent: Nov. 28, 2017

(54) NANOPORE STOCHASTIC SENSING OF BIOMARKERS

(71) Applicants: Xiyun Guan, Oak Brook, IL (US); Liang Wang, Chicago, IL (US); Shuo Zhou, Chicago, IL (US)

(72) Inventors: Xiyun Guan, Oak Brook, IL (US); Liang Wang, Chicago, IL (US); Shuo Zhou, Chicago, IL (US)

(73) Assignee: Illinois Institute of Technology, Chicago, IL (US)

( * ) Notice: Subject to any disclaimer, the term of this patent is extended or adjusted under 35 U.S.C. 154(b) by 0 days.

(21) Appl. No.: 14/657,810

(22) Filed: Mar. 13, 2015

(65) Prior Publication Data
US 2015/0259724 A1 Sep. 17, 2015

Related U.S. Application Data

(60) Provisional application No. 61/952,554, filed on Mar. 13, 2014.

(51) Int. Cl.
*C12Q 1/37* (2006.01)
*G01N 33/487* (2006.01)
*C12Q 1/68* (2006.01)

(52) U.S. Cl.
CPC ............ *C12Q 1/37* (2013.01); *C12Q 1/6825* (2013.01); *G01N 33/48721* (2013.01)

(58) Field of Classification Search
CPC ...................................................... C12Q 1/37
See application file for complete search history.

(56) References Cited

PUBLICATIONS

Liu, A., et al., "Unxipping of Double-Stranded DNA in Engineered α-Hemolysin Pores," J. Phys. Chem. Lett., May 2011, vol. 2, pp. 1372-1376.

Zhao, Q., et al., "Real-Time Monitoring of Peptide Cleavage Using a Nanopore Probe," J. Am. Chem. Soc., Apr. 2009, vol. 131, pp. 6324-6325.
Kang, X., et al., "Stochastic Detection of Enantiomers," J. Am. Chem. Soc., Jul. 2006, vol. 128, pp. 10684-10685.
Siwy, Z., et al., "Protein Biosensors Based on Biofunctionalized Conical Gold Nanotubes," J. Am. Chem. Soc., Mar. 2005, vol. 127, pp. 5000-5001.
Gu, L., et al., "Stochastic Sensing of Organic Analytes by a Pore-Forming Protein Containing a Molecular Adapter," Nature, Apr. 1999, vol. 398, pp. 686-690.
Zhao, Q., et al., "Study of Peptide Transport Through Engineered Protein Channels," J. Phys. Chem. B, Feb. 2009, vol. 113, pp. 3572-3578.
Wang, G., et al., "Nanopore Stochastic Detection: Diversity, Sensitivity, and Beyond," J. Am. Chem. Soc., Apr. 2013, vol. 46, No. 12, pp. 2867-2877.

*Primary Examiner* — Maryam Monshipouri
(74) *Attorney, Agent, or Firm* — Pauley Erickson & Kottis

(57) ABSTRACT

A method and system for sensing or characterizing a biomarker, such as a proteolytic enzyme or nucleic acid. The system comprises a nanopore sensor to determine a current modulation of a sample including a biomarker, and a predetermined substrate or nucleic acid probe current modulation signature for comparison to a current signature from the nanopore sensor. The nanopore sensor includes a nanopore membrane between two fluid compartments, and a power supply in electrical contact with the membrane to provide an electric potential difference between the fluid compartments. A detector is used to detect an electrical current through the nanopore as the polypeptide substrate, or components thereof, transits the nanopore under an applied electric potential difference between the first and second fluid compartments. The result is a rapid, label-free method for the sensitive and accurate measurement of biomarker activity by real-time monitoring of the ionic current modulations arising from the substrate peptide-protease interactions or nucleic acid hybridization in the nanopore.

16 Claims, 10 Drawing Sheets

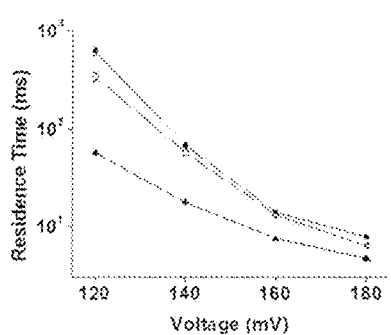
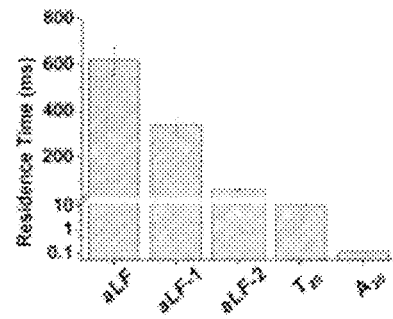
FIG. 17   FIG. 18
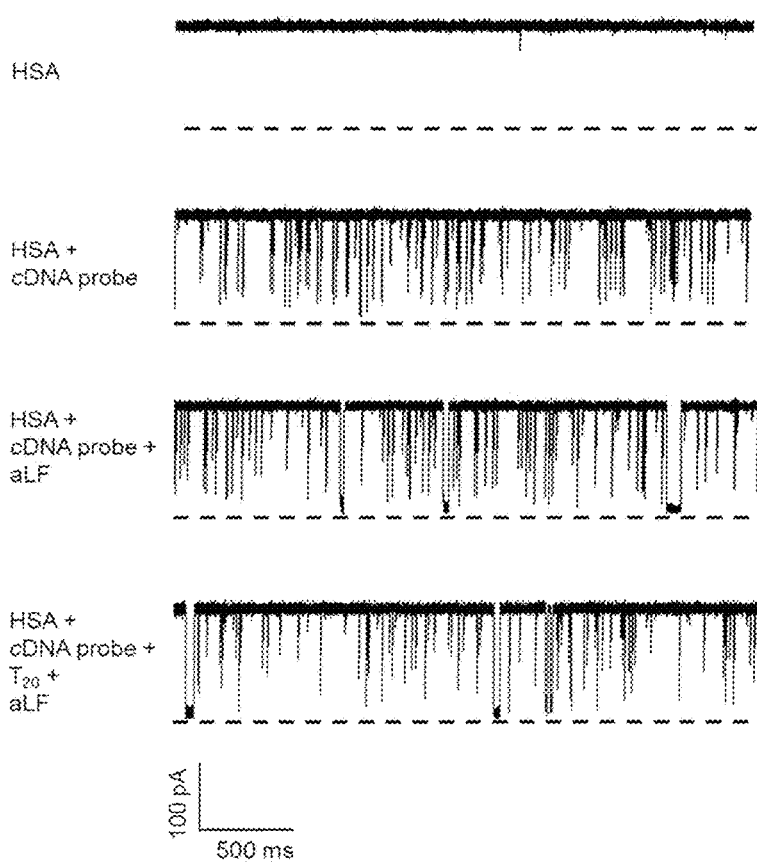
FIG. 19

NANOPORE STOCHASTIC SENSING OF BIOMARKERS

CROSS REFERENCE TO RELATED APPLICATION

This application claims the benefit of U.S. Provisional Patent Application, Ser. No. 61/952,554, filed on 13 Mar. 2014. The co-pending Provisional Patent Application is hereby incorporated by reference herein in its entirety and is made a part hereof, including but not limited to those portions which specifically appear hereinafter.

GOVERNMENT SUPPORT CLAUSE

This invention was made with government support under Grant/Contract Number(s) GM110632 awarded by the National Institutes of Health. The government has certain rights in the invention.

FIELD OF THE INVENTION

This invention relates generally to detecting biomarkers and, more particularly, to an apparatus and method for detecting and/or characterizing proteolytic enzymes or other biomarkers for a wide variety of applications, such as common diseases, infectious diseases, cancer, food safety, biodefense, etc.

BACKGROUND OF THE INVENTION

A biomarker, or biological marker, generally refers to a measurable indicator of some biological state or condition. Certain biochemical components, such as enzymes, proteins, nucleic acids, lipids, etc., can be used as biomarkers for the presence of the biological entity or condition (e.g., virus, bacteria, damaged cell, etc.) that created the biomarkers. The detection of the biomarker component can be used to detect the presence of the producing entity. As an example, a proteolytic enzyme, also referred to as a protease, peptidase, or proteinase, is an enzyme that performs proteolysis, or protein catabolism by hydrolysis of the peptide bonds that link amino acids together in the polypeptide chain forming the protein. The presence of particular proteolytic enzymes can be indicators of particular conditions. As a specific example, the HIV-1 protease is a retroviral aspartyl protease, and has been recognized as an essential element in maturation of the infectious virus. Accordingly, HIV-1 protease has been an important target for drug therapy.

At present, the majority of the developed methods for HIV detection are based on the detection of the presence of antibodies that the patient's body makes against HIV, direct molecular recognition of HIV and its components such as specific nucleic acid sequences or antigens, or measurement of the activity of HIV-1 protease, many of which are often laborious and time-consuming, and/or require the use of labels or sophisticated instruments.

There is a continuing need for improved detection of common and/or infectious diseases or conditions.

SUMMARY OF THE INVENTION

A general object of the invention is to provide an apparatus and method for detecting biomarkers, such as proteins, enzymes or nucleic acids (RNA or DNA), for a wide variety of applications, such as common diseases, infectious diseases, cancer, food safety, pharmaceutical screening, environmental protection, biodefense, etc.

The general object of the invention can be attained, at least in part, through a method for sensing or characterizing biomarkers, such as proteins, enzymes or nucleic acids. The method includes providing two fluid compartments separated by an electrically resistant membrane bilayer including a nanopore, introducing a sample, such as containing a substrate or nucleic acid probe, to a first fluid compartment, and applying an electric field across the membrane. A current modulation signature of the sample is monitored across the membrane, from which a presence of a biomarker in the sample can be determined as a function of the sample current modulation signature. If the biomarker is present, the target substrate or nucleic acid probe within a first of the fluid compartments is modified, such as by enzyme cleavage or hybridization, resulting in a change in the ionic current passing through the nanopore. The presence of the biomarker can be determined by comparing the sample current modulation signature to a known substrate current modulation signature for the non-cleaved polypeptide substrate and/or sample.

The invention further includes a system for sensing or characterizing a proteolytic enzyme. The system comprises a nanopore sensor to determine a current modulation of a sample including a polypeptide substrate, and a predetermined substrate current modulation signature for comparison to a current signature from the nanopore sensor. The nanopore sensor includes two fluid compartments, with a membrane separating the first fluid compartment and the second fluid compartment. A nanopore through the membrane fluidically connects the first compartment and the second compartment, and a power supply in electrical contact with the membrane provides an electric potential difference between the fluid compartments. A detector is used to detect an electrical current through the nanopore as the polypeptide substrate, or components thereof, transits the nanopore under an applied electric potential difference between the fluid compartments.

The present invention includes a rapid, label-free method for the sensitive and accurate measurement of protease activity by real-time monitoring of the ionic current modulations arising from the substrate peptide-protease interactions in a nanopore. This method is rapid and sensitive: picomolar concentrations of protease can be accurately detected in approximately 10 minutes. Further, the protease assay does not require the use of expensive equipment. The substrate-based nanopore sensing approach is useful for nanopore sensors of various proteolytic enzymes, such as, without limitation, HIV protease, HCV protease, metalloprotease, such as matrix metalloproteinases (MMPs) and a disintegrin and metalloproteinases (ADAMs), serine protease (e.g., trypsin), cysteine protease, threonine protease, aspartic protease, etc.

Embodiments of this invention provide a rapid, sensitive, and label-free nanopore sensing apparatus and method for the detection of various proteases. In embodiments of this invention, a protease target compound is utilized as the sensing element, while an unmodified peptide is used as the substrate. Under a fixed potential bias applied across the nanopore membrane, the activity of the protease can be detected and quantified by monitoring the change in the ionic current passing through the nanopore, which is due to the cleavage of the peptide by the protease. The method is sensitive (can detect protease at pico- to nanomolar levels) and selective (other proteases will not interfere with the detection).

The nanopore sensor of this invention can be incorporated in the development of cost-effective stochastic sensors for proteases of medical and biological importance. Such sensors not only have potential clinical values for diagnosis or prognosis of infectious diseases, cancer, and cardiovascular diseases, but also could be utilized for drug discovery and development.

Other objects and advantages will be apparent to those skilled in the art from the following detailed description taken in conjunction with the appended claims and drawings.

DESCRIPTION OF THE DRAWINGS

FIG. 17 shows the effect of the applied voltage bias on the mean residence time of the DNA duplex events for (■) aLF, (○) aLF-1, and (▲) aLF-2.

FIG. 18 summarizes selectivity data of an aLF nanopore sensor according to one embodiment of this invention.

FIG. 19 shows representative trace segments of HSA alone and mixtures of HSA and other DNA molecules.

DETAILED DESCRIPTION OF THE INVENTION

The present invention provides a real-time nanopore sensing method and system for the sensitive detection or characterization of a biomarker. The invention can be used for detection of various biomarkers, such as proteins, enzymes, nucleic acids (e.g., RNA or DNA), lipids, etc., but will be generally discussed below referring to proteolytic enzymes.

Nanopore detection is achieved by monitoring ionic current modulations produced by the passage of target analytes through one or more nanopores. Under conditions of constant electrolyte pH, temperature, and applied potential, the extent of current blockage (amplitude) is related to the size/diameter of the analyte molecule, while the event residence time depends on the length of the analyte and the strength of the interaction between the analyte and the nanopore. Since analytes pass through a nanopore at one molecule at a time, the event frequency can be correlated with the concentration of the analyte, and simultaneous quantification of multiple components in a solution mixture can be readily accomplished using a single nanopore as long as the nanopore itself can provide enough resolution.

The invention provides methods and systems for detecting protease activity. In addition to monitoring peptide-protease interaction, the invention can be used to obtain quantitative chemical kinetics information on the enzymatic process. The invention can also be used for recognition of peptides, including differences of one or more amino acids. In general, with an increase in the length of the peptide, both the amplitude and residence time of the events increase. With an appropriately engineered αHL nanopore, the invention can discriminate between peptides having the same length and composition but possessing different sequences. The findings suggest that nanopore sensing technology has the potential to be utilized for protein sequencing. Another advantage of the nanopore sensing of this invention is that multiple components in a solution mixture can be quantitated simultaneously using a single nanopore because analytes interact with the nanopore at one molecule at a time. Short peptide fragments, obtained from protease cleavage of a longer substrate peptide, can thus be identified and even quantified by the nanopore sensor without the need for separation and purification.

Figure 1:
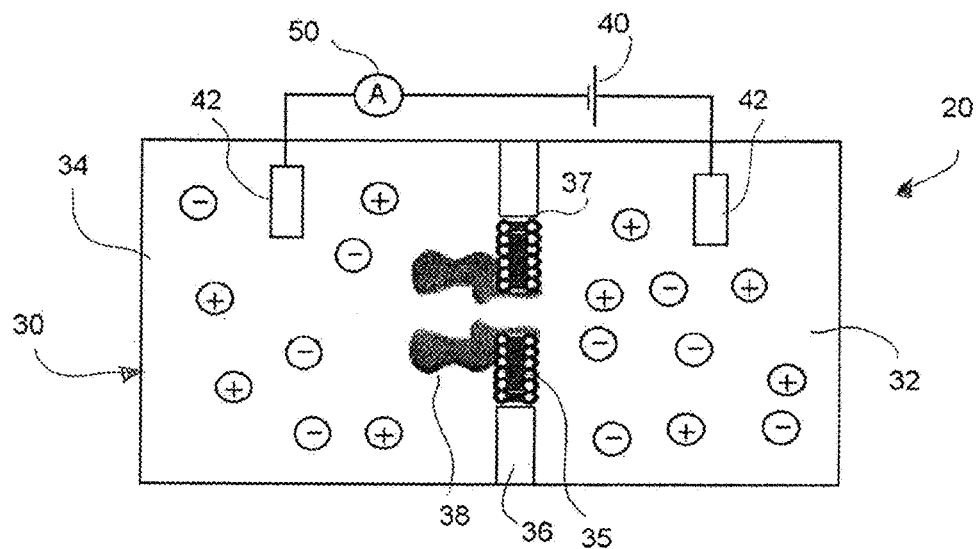
FIG. 1 is a schematic representation of a nanopore sensor device according to one embodiment of this invention.

FIG. 1 is a schematic representation of a system 20 for sensing or characterizing a proteolytic enzyme, according to one embodiment of this invention. The system includes a nanopore sensor 30, such as shown FIG. 2, to determine a current modulation of a sample including a polypeptide substrate. The sensor 30 includes a first fluid compartment 32, such as a trans compartment, and a second compartment 34, such as a cis compartment, separated by a membrane 36 with an aperture 37. The compartments 32, 34 can be filled with any suitable solution, such as a sodium chloride solution. The membrane 36, or septum, can be formed of any suitable material, such as PTFE, for dividing a chamber into the trans and cis compartments 32 and 34. The aperture 37 of the membrane 36 can be sized as needed, such as about 100-200 µm, and more preferably about 150 µm. A bilayer 35 of 1,2-diphytanoylphosphatidylcholine, or other suitable alternative, will be formed across the aperture 37. At least one, and desirably only one, nanopore 38 inserts through the bilayer 35, and connects the first compartment 32 and the second compartment 34.

Figure 2:
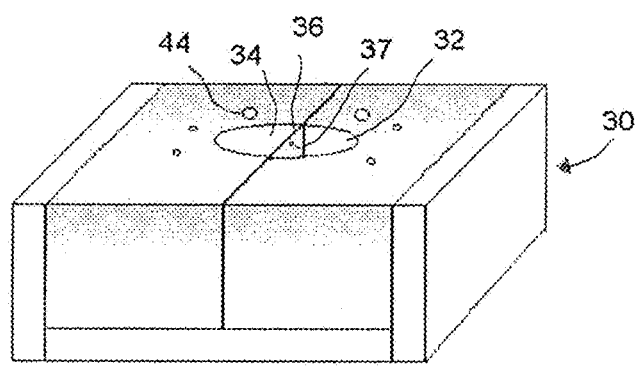
FIG. 2 illustrates a nanopore sensor device according to one embodiment of this invention.

A power supply 40 is connected in electrical contact with the sensor 30 and the membrane 36 to provide an electric potential difference between the first fluid compartment 32 and the second fluid compartment 34. The power supply 40 can connect to the sensor by electrodes 42, such as Ag/AgCl electrodes, each in electrical combination with one of the first fluid compartment 32 and the second fluid compartment 34. As shown in FIG. 2, the sensor 30 can have electrode attachment points 44, such as holes or openings for receiving a corresponding one of the electrodes 42.

A detector 50 is used to detect an electrical current through the nanopore 38 as the polypeptide substrate, or components thereof, transits the nanopore 38 under an applied electric potential difference between the first and second fluid compartments 32, 34. Under a fixed potential bias applied across the nanopore membrane 36, the activity of the protease can be detected and quantified by monitoring the change in the ionic current passing through the nanopore, which is due to the cleavage of the target analyte substrate, such as a peptide, by the protease.

Figure 3:
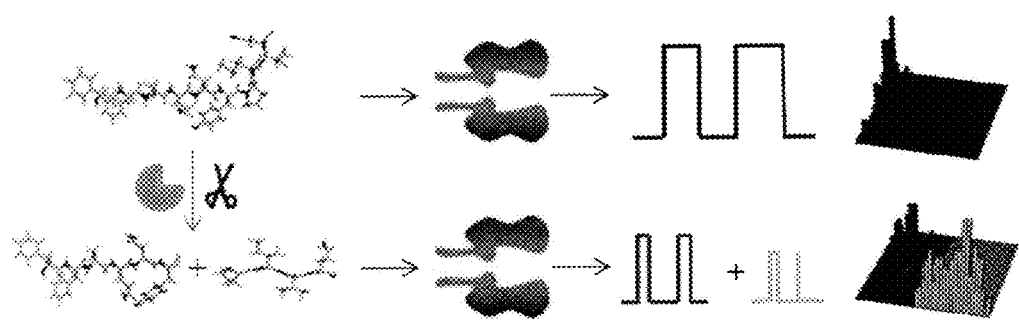
FIG. 3 is a schematic representation of the principle for nanopore detection of the activity of protease according to one embodiment of this invention.

According to embodiments of this invention, a sample is introduced to the first fluid compartment 32. An electric field is applied across the membrane 36, such as a fixed applied potential, to drive a target analyte substrate through the nanopore 38. By the detector 50, a current modulation signature across the membrane 36 is monitored and determined, and from the current modulation signature a presence of a proteolytic enzyme in the sample can be determined. As illustrated in FIG. 3, the presence of the proteolytic enzyme results in a change in the current modulation signature of the sample by cleaving a target chemical compound, such as a polypeptide, within the sample. In one embodiment of this invention, the polypeptide substrate has a predetermined, known substrate current modulation signature, and the determination of a presence of a proteolytic enzyme in the sample is performed by comparing the sample current modulation signature obtained by the detector 50 to the known substrate current modulation signature. A difference between the sample current modulation signature and the known substrate current modulation signature indicates the presence of the proteolytic enzyme.

In embodiments of this invention, the polypeptide substrate can include more than one cleavage site, each cleaved by one of two or more different proteolytic enzymes. The predetermined substrate current modulation signature can correspond to cleavage products of one or both of the two different proteolytic enzymes, thereby identifying one or more of the multiple enzymes. The presence of each of the multiple different proteolytic enzymes alone and/or a combination of the two different proteolytic enzymes in the sample can be determined by comparing the sample current modulation signature to the known substrate current modulation signature. For example, take a peptide substrate containing two cleavage sites, each corresponding to one of two different proteases, if only one protease is present in the sample, the substrate will be cleaved into two fragments. Therefore, the observation of two new types of current modulations indicates the presence of one protease in the sample. Furthermore, by comparing the signatures of these new events with those of the predetermined peptide fragments, the identity of the protease can be determined. If two proteases are present in the sample, three fragments will be produced from the proteolytic cleavage of the substrate.

In one embodiment of this invention, a target analyte is added with the sample to the sensor compartment. The added analyte can be a natural substrate or a modified substrate, such as a modified or engineered polypeptide including one or more additional amino acids, for a target proteolytic enzyme. The modified polypeptide substrate can provide cleavage segments of different lengths upon contact with the proteolytic enzyme. The known cleavage segments will produce predictable current modulation signatures in the sensor, thereby indicating the presence of the enzyme in the sample.

The method and system of this invention can also be used to determine a concentration of the proteolytic enzyme and/or a polypeptide substrate. In one embodiment, the concentration can be determined by a frequency of occurrence of nanopore blockage events within the sensor. By monitoring the ionic current modulations produced by the passage of the target analyte through a single nanopore at a fixed applied potential, the concentration of the analyte can be obtained by the frequency of occurrence ($1/\tau_{on}$) of the blockage events, while its identity can be determined from the mean residence time ($\tau_{off}$) of the analyte coupled with the extent of current blockage (amplitude). Under experimental conditions of constant electrolyte pH, temperature, and applied potential bias, the event blockage amplitude is related to the size, structure, and/or conformation of the analyte molecule, while the event residence time depends on the length of the analyte and the strength of the interaction between the analyte and the nanopore. In addition to biosensing, nanopore analysis can be utilized for a variety of other applications, including studying covalent and non-covalent bonding interactions, investigating biomolecular conformational changes, probing enzyme kinetics, and so on.

The method and system of this invention can be used to detect various enzymes, and can be applied for any suitable detection purposes, such as, without limitation, for medical purposes, food safety purposes, and/or biodefense purposes. As one example, the method and system can be used to detect infections and/or diseases. In one embodiment of this invention, an infection is determined by identifying the presence of proteolytic enzymes in a sample that are known to be produced by a pathogen during such an infection. In a similar embodiment, a disease can be identified by identifying the presence of proteolytic enzymes in a sample that are known to be produced by diseased cells, such as cancer cells.

In one embodiment of this invention, the method and system are used to determine the presence of a retroviral infection, such as HCV or HIV, by determining the presence of a retroviral aspartyl protease in a patient sample. As one example, the activity of HIV protease is measured by real-time monitoring of the ionic current modulations arising from the substrate-protease interactions. As shown in FIG. 3, in the absence of HIV-1 protease, the peptide substrate produces only one major type of current modulation events during translocation through the nanopore. However, in contrast, in the presence of the protease, the substrate is cleaved into two fragments. Since the substrate breakdown products have shorter lengths than the substrate, new blockage events having smaller residence times ($\tau_{off}$) and/or amplitudes from those of the substrate are observed. By monitoring the frequency or counts of the produced new events, the activity of HIV-1 protease can be quantified. With a constant substrate concentration and a fixed amount of recording (i.e., reaction) time, the concentration and hence the event frequency of the produced substrate cleavage products or the remaining substrate depends on the activity of the HIV protease.

In another embodiment of this invention, the method and system provide a biosensor to measure proteolytic enzymes as an indicator for disease. As an example, trypsin is a serine protease which cleaves peptide bonds after arginine or lysine amino acid residues. Patients suffering from acute pancreatitis exhibit higher concentrations of trypsin than healthy people, thereby making trypsin a useful biomarker for pancreatitis. In one embodiment of this invention, a rapid and sensitive method for the detection of trypsin is provided by using a biological alpha-hemolysin nanopore. Due to a larger molecular diameter than a narrow pore constriction, trypsin cannot transport through the alpha-hemolysin channel. Hence, an indirect detection method is developed by using a lysine-containing peptide as the substrate, and analyzing the cleavage products of the substrate after trypsin digestion.

As another example, the invention includes a nanopore sensor system for detecting cancer. Matrix metalloproteinases (MMPs) and a disintegrin and metalloproteases (ADAMs) are considered biomarkers and potential therapeutic targets in human cancers. MMPs are a family of more than 20 zinc-dependent endopeptidases that share a similar structure, and are collectively capable of degrading all components of the extracellular matrix and basement membrane. They play important roles in cell biological processes and many fundamental physiological events involving tissue remodeling, such as angiogenesis, bone development, wound healing, and mammary involution. However, dysregulated activities of MMPs may lead to a number of pathological conditions such as tumor growth, invasion, and metastasis, rheumatoid arthritis, and heart failure. ADAMs are a family of more than 30 integral membrane and secreted glycoproteins that are related to snake venom metalloproteases and MMPs. Elevated activity levels of MIVIPs and/or ADAMs have been observed in almost every type of human cancer, and found to correlate with advanced tumor stage, increased invasion and metastasis, and shortened survival. MMPs and ADAMs can serve as valuable biomarkers for early diagnosis and prognosis in human cancers, and are becoming increasingly important targets for drug discovery and cancer therapy.

Embodiments of this invention provide a sensitive, selective, cost-effective, and, optionally, multiplexed sensing platform to profile the activities of MMPs/ADAMs for early cancer detection and diagnosis. The method and apparatus can operate by measuring protease activities based upon the increase in the concentration of the target degradation products of the substrate. With this strategy provided by this invention, the generated different peptide fragments allow the differentiation between the target MMP/ADAM and false positives, resulting from the common occurrence of non-target proteases and the target MMP/ADAM cleaving the substrate peptide at different positions.

In one embodiment, a panel of MMPs/ADAMs can be detected instead of a single protease as cancer biomarkers to improve cancer diagnostic accuracy. For this purpose, the invention includes multiplex nanopore sensor platforms for the concurrent measurement of the activities of multiple MMPs/ADAMs. The ability to measure the activities of multiple MMPs/ADAMs in a single assay has many advantages over singleplex systems, including reduced assay costs, improved turnaround time, reduced sample/reagent volume, high-throughput screening, and decrease in errors between inter-sampling. An added advantage of measuring protease activities by monitoring the substrate degradation products is that multiplex detection of the activities of multiple MMPs/ADAMs can be readily accomplished by using a single nanopore and a single substrate containing multiple cleavage sites for different proteases instead of the conventional sensor array format, thus further reducing the up-front costs of the protease assays (due to fabrication and use of fewer nanopores).

Measuring the activities of MMPs/ADAMs can be achieved by real-time monitoring of the ionic current modulations caused by the protease-peptide interactions in the nanopore. In the absence of proteases, the current modulations are caused only by the substrate. However, in sharp contrast, in the presence of the target protease, the substrate will be cleaved into two or more fragments (depending on the number of the substrate cleavage sites). Since the substrate breakdown products have shorter lengths than the substrate, new blockage events having smaller residence times and/or blockage amplitudes than those of the substrate may be observed. Furthermore, with a constant initial substrate concentration and a fixed amount of reaction time, the concentration and hence the event frequency of the substrate breakdown products depend on the activity of the protease. As discussed above, in the case that other proteases can also cleave the same substrate but at different positions, the substrate cleavage site allows the target MMP/ADAM to be differentiated from other proteases based on their produced quite different substrate breakdown products and their corresponding events with different signatures, thus improving the selectivity of the protease sensor.

Embodiments of this invention include label-free, real-time nanopore sensing methods and systems for the detection of nucleic acid biomarkers (e.g., DNA or RNA) using nucleic acid probes. The method is again rapid and sensitive: picomolar concentrations of the target biomarker nucleic acid could be detected rapidly, such as in approximately 1 minute. Further, the method is selective, which can differentiate the target nucleic acid DNA from other single-stranded nucleic acid molecules at the single-base resolution. This sequence-specific detection according to this invention can be particularly useful in nanopore sensors for, without limitation, pathogens.

In embodiments of this invention, the nanopore detection of pathogens or other diseases is based on the hybridization between a characteristic single-stranded gene segment of the target pathogen and an unmodified complementary single-stranded DNA (cDNA) probe. Although their diameters are typically larger than the channel constriction, short double-stranded DNA (dsDNA) molecules can be rapidly unzipped through an appropriately engineered α-hemolysin (αHL) protein nanopore. The nanopore can be engineered with functional groups, such as by introducing positively charged or aromatic groups into the nanopore, to facilitate unzipping of dsDNA.

Figure 15:
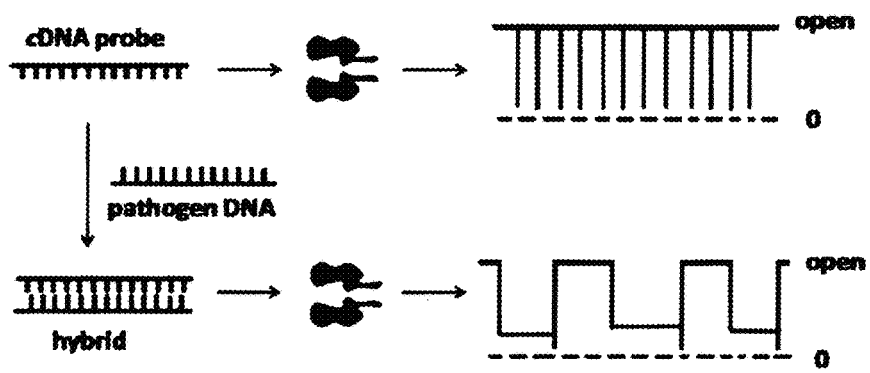
FIG. 15 representatively illustrates the hybridization of a target pathogen gene segment by an unlabeled complementary DNA probe to produce current modulation events in the nanopore having significantly different signatures from those of the cDNA probe.
Figure 16:
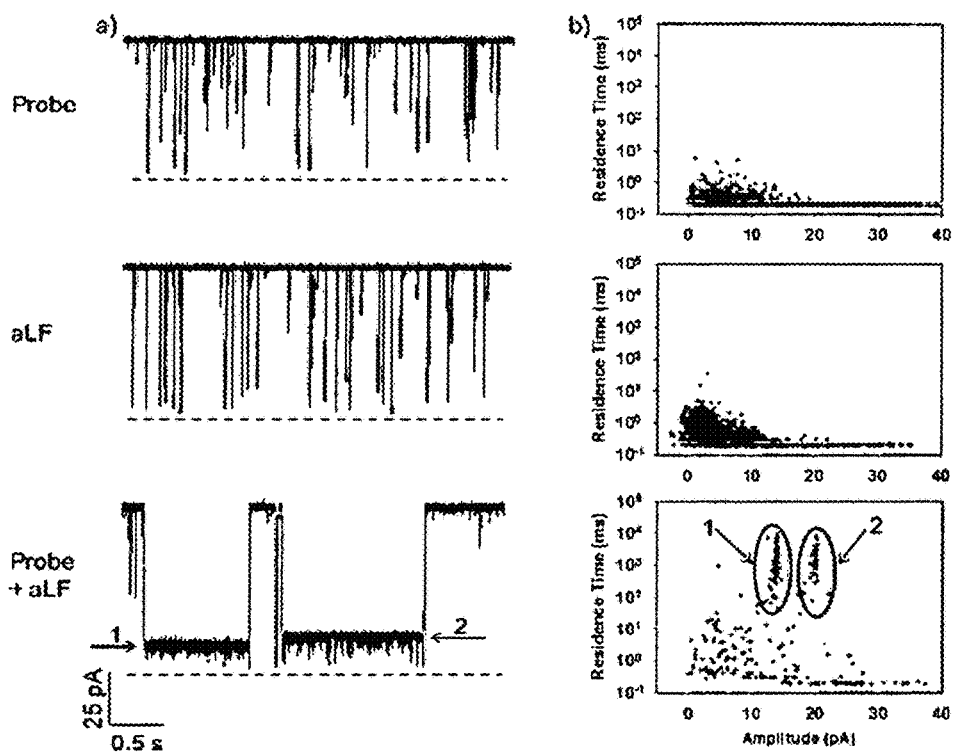
FIG. 16 shows the hybridization of the target aLF strand by the cDNA probe: (a) representative single-channel current recording trace segments, and (b) the corresponding scatter plots of event residence time vs. amplitude.

As shown in FIG. 15, in the absence of the target pathogen gene segment, the translocation of the cDNA probe through the nanopore produces only one major type of current modulation events. In contrast, in the presence of the target DNA sequence, two complementary DNA monomers will be hybridized in the solution to form dsDNA molecules. Due to their larger molecular sizes than those of ssDNA molecules, the interaction between the dsDNA and the nanopore can result in a new type of current modulation events having different signatures from those of the cDNA probe and the single stranded pathogen gene segment, e.g., with longer residence times and/or showing complicated sub-state current modulation features.

The invention provides or includes probes that form blunt-end ds-DNA with the target DNA, without less desirable overhangs. In one embodiment, the nucleic acid probe will form relatively long (e.g., 20 bp) full-matched blunt-ended dsDNA with the target nucleic acid biomarker. The method is thus more accurate, which is important in medical diagnosis.

The present invention is described in further detail in connection with the following examples which illustrate or simulate various aspects involved in the practice of the invention. It is to be understood that all changes that come within the spirit of the invention are desired to be protected and thus the invention is not to be construed as limited by these examples.

EXAMPLES

HIV-1 Protease Sensor

A nanopore sensing apparatus for the detection of HIV-1 protease was created, in which an engineered alpha-hemolysin was utilized as the sensing element, while an unmodified peptide was used as the substrate. Under a fixed potential bias applied across the nanopore membrane, the activity of the HIV-1 protease was detected and quantified by monitoring the change in the ionic current passing through the nanopore, which is due to the cleavage of the peptide by the HIV-1 protease. The method was sensitive (detected HIV-1 protease at pico- to nanomolar levels) and selective (other proteases did not interfere with the detection).

A HIV-1 protease substrate peptide with a sequence of FFSQNYPIVQ (>98% pure) was purchased from Biomatik Corporation (Wilmington, Del.), while the HIV-1 protease was ordered from BioVendor Lab (Brno, Czech Republic). All the other chemicals were obtained from Sigma-Aldrich (St. Louis, Mo.). The peptide, protease, and chemicals were dissolved in HPLC-grade water (ChromAR, Mallinckrodt Baker). The stock solutions of the peptide and the protease were prepared at 10 mM, and 300 µg/mL, respectively, and were kept at −80° C. before and after use. The electrolyte used contained 1.0 M NaCl buffered with 1 mM EDTA and 1 mM $NaH_2PO_4$, with the pH adjusted to 4.7 using $H_3PO_4$ solution. Lipid 1,2-diphytanoylphosphatidylcholine was obtained from Avanti Polar Lipids (Alabaster, Ala.). Teflon film (25 µm thick) was purchased from Goodfellow (Malvern, Pa.).

To prepare the protein nanopore, the mutant αHL M113F gene was constructed by site-directed mutagenesis (Mutagenex, Piscataway, N.J.) with a wild-type αHL gene in a T7 vector (pT7-αHL). The mutant αHL monomers were first synthesized by coupled in vitro transcription and translation (IVTT) using the *E. Coli* T7 S30 Extract System for Circular DNA from Promega (Madison, Wis.). Subsequently, they were assembled into homoheptamers by adding rabbit red cell membranes and incubating for 1-2 hours. The heptamers were then purified by SDS-polyacrylamide gel electrophoresis and stored in aliquots at −80° C.

A bilayer of 1,2-diphytanoylphosphatidylcholine was formed on an aperture (150 µm) in a Teflon septum that divided a planar bilayer chamber into cis and trans compartments, such as shown above FIG. 2. The formation of bilayer was achieved using the method of M. Montal and P. Mueller, *Proc. Nat. Acad. Sci.*, 1972, 69, 3561-3566. Unless otherwise noted, all the experiments were performed under a series of symmetrical buffer conditions with a 2.0 mL solution comprising 1 M NaCl, 1 mM EDTA, and 10 mM $NaH_2PO_4$ (pH 4.7) at 26±1° C. The αHL protein was added to the cis compartment, which was connected to "ground", while the peptide substrate and HIV-1 protease were added to the trans compartment. The final concentration of the αHL proteins used for the single channel insertion was 0.2-2.0 ng/ml$^{-1}$. Currents were recorded with a patch clamp amplifier (Axopatch 200B, Molecular Devices; Sunnyvale, Calif., USA). The currents were low-pass filtered with a built-in four-pole Bessel filter at 5 KHz and sampled at 50 KHz by a computer equipped with a Digidata 1322A/D converter (Molecular Devices).

Data were analyzed with the following software: pClamp 10.3 (Molecular Devices), Origin 8.0 (Microcal, Northampton, Mass.), and SigmaPlot 12.0 (Systat Software Inc., San Jose, Calif.). Conductance values were obtained from the amplitude histograms after the peaks were fit to Gaussian functions. Values of $\tau_{on}$ and $\tau_{off}$ for the peptide events were obtained from the open state (1) and close state (0) dwell time histograms, respectively by fitting the distributions to single exponential functions by the Levenberg-Marquardt procedure. The event frequency (f) was calculated by using the equation $f=1/\tau_{on}$.

Initial experimentation was carried out at an applied potential bias of −40 mV in an electrolyte solution comprising 1 M NaCl, 1 mM EDTA and 1 mM $NaH_2PO_4$ (pH 4.7). This voltage has been demonstrated appropriate for nanopore peptide analysis, while pH 4.7 is the optimum solution pH for the detection of HIV-1 protease. As mentioned above, the nanopore sensing element used was a mutant α-hemolysin (αHL) protein, (M113F)$_7$, while a peptide having a sequence of FFSQNYPIVQ was employed as the substrate. It has been shown that the αHL (M113F)$_7$ protein could provide an enhanced resolution (e.g., prolonged residence time) for (bio-)molecule recognition compared with that observed with the wild-type αHL pore. Note that in the substrate design, two additional Phe amino acids were added to the sequence of a well-known HIV-1 protease substrate, SQNYPIVQ, for the purpose of creating two cleavage segments (i.e., FFSQNY and PIVQ) with different lengths. Unlike various conventional enzyme assays which detect the enzyme activity predominantly based on the signal decrease in the substrate, this nanopore sensor measured the HIV-1 protease activity based on the signal increase in the substrate degradation products. One significant advantage of such a sensor design strategy is that other interfering proteases (i.e., false positives) could be differentiated from the target HIV-1 protease if they cleave the peptide substrate at different positions, thus improving the sensor accuracy and selectivity. Since the molecular size (with dimensions of 45×23×25 Å) of the HIV-1 protease (a 99 amino acid aspartyl protease that functions as a homodimer with only one active site) is larger than that of the protein pore transmembrane domain (20 Å diameter), it could not enter the nanopore and hence could not produce current blockage events that might interfere with the identification of the target peptide(s) (See FIG. 6).

Figure 4:
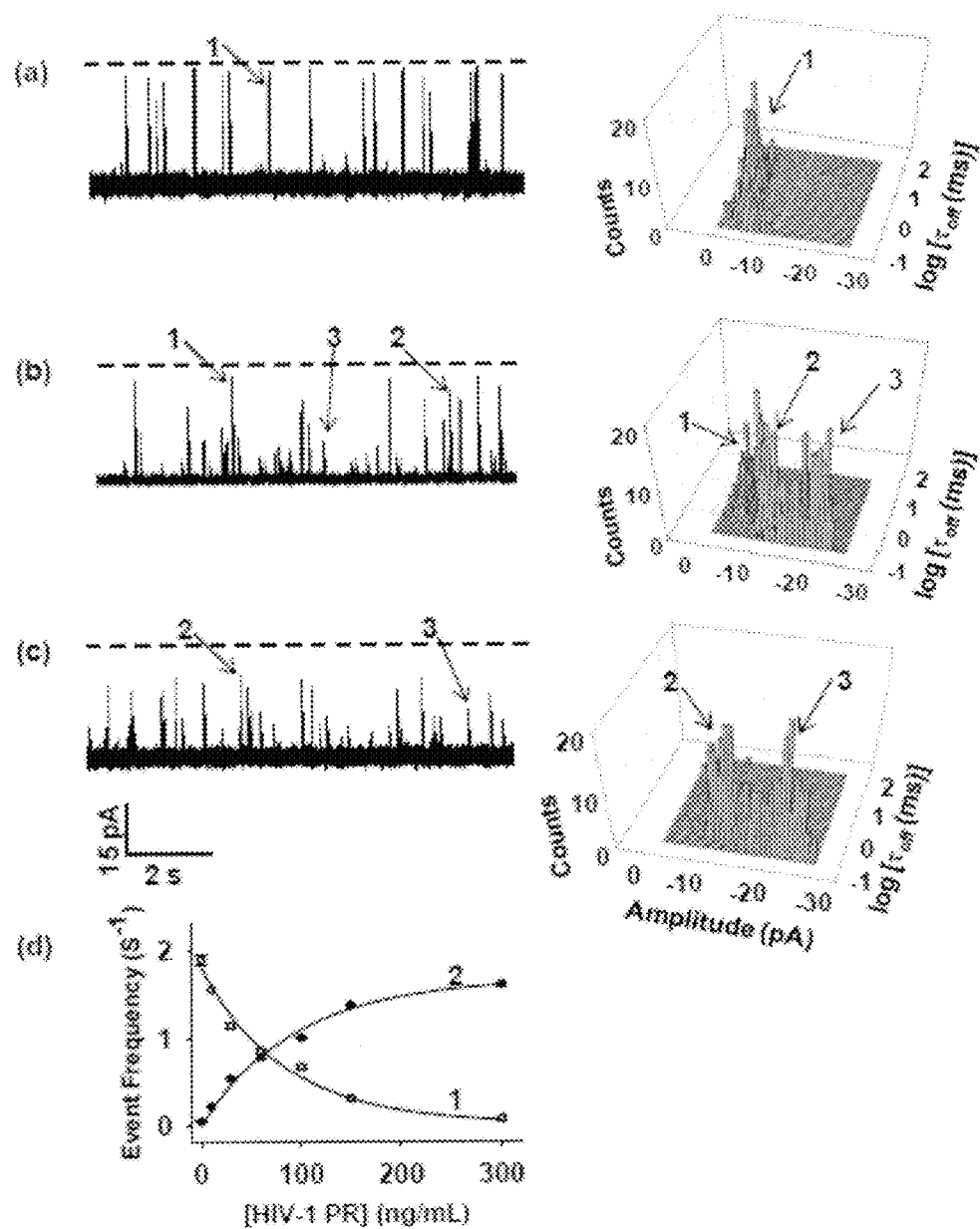
FIG. 4 shows measurements of the activity of HIV-1 protease in a nano-cavity: typical single-channel current recording trace segments after 55 min proteolytic reactions for (a) 0 ng/mL HIV-1 PR; (b) 60 ng/mL HIV-1 protease; and (c) 300 ng/mL HIV-1 PR; (d) is a plot of event frequency versus the concentration of HIV-1 protease.

Referring to FIG. 4, experimental results showed that, in the absence of the HIV-1 protease, the buffer solution containing the substrate peptide produced only one major type of current blockage with a mean residual current around −3.5 pA (FIG. 4*a*). In FIG. 4, dashed lines represent the levels of zero current. The corresponding 3D plots of event count vs. residence time vs. blockage amplitude are shown on the right. Labels 1, 2, and 3 in FIGS. 4*a-c* represent events attributed to the substrate, and the two degradation products, respectively. FIG. 4d is a plot of event frequency versus the concentration of HIV-1 PR. Labels 1 and 2 represent the substrate and the cleavage product, respectively. The experiments were performed by real-time monitoring the substrate-protease interaction continuously for 1 h at −40 mV in 1 M NaCl solution buffered with 1 mM EDTA and 1 mM $NaH_2PO_4$ (pH 4.7). The concentration of the substrate peptide was 5 µM. Event counts and event frequency in FIGS. 4a-d were calculated based on the last 5 min trace segment of a 60 min single channel recording.

Upon addition of HIV-1 protease to the solution, two new types of blockage events having mean residual currents of −9.5 pA, and −18.0 pA were observed (labeled as "type 2" and "type 3" events in FIGS. 4b and 4c). Note that in addition to their amplitude difference, these two new types of events also showed significantly different residence times. Furthermore, with an increase in the concentration of the added protease, the event frequency of the new events increased, while that of the substrate decreased, clearly suggesting that the new events are attributed to the proteolytic cleavage process, specifically from the produced two fragments FFSQNY and PIVQ.

It should be noted that since the smaller amplitude blockage events of the substrate degradation products partially overlapped with the background current spikes (~one event per ten seconds) of the (M113F), pore, only the larger amplitude new type of (i.e., type 2) events were included in the data analysis of the event frequency. The detection limit (defined as the concentration corresponding to three times the standard deviation of a blank signal) for HIV-1 protease in a 1 hour enzymatic reaction was 0.47 ng/mL (equivalent to 47 pM).

Figure 7:
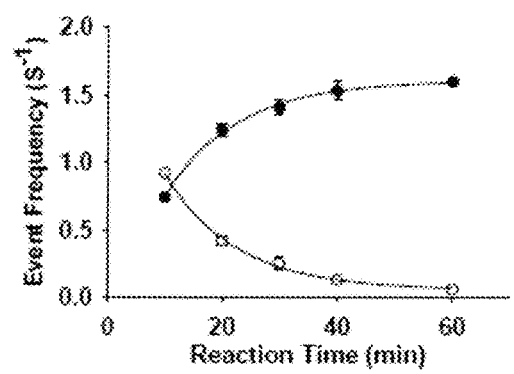
FIG. 7 is a graph of the effect of reaction time on the event frequency of the peptide substrate (○) and its degradation product (●).

To examine whether sensitive detection of HIV-1 protease could be achieved rapidly, the effect of the monitoring time (i.e., the reaction time) on the detection limit for protease detection was systematically studied. It should be noted that, in a proteolytic reaction, the instantaneous concentrations and hence the event frequencies of the substrate and the degradation products vary with the reaction time until all the substrate is degraded (FIG. 7). For FIG. 7, the event frequency at a particular time point t (min) was obtained based on the statistical analysis of all the events collected during the period from time point t−10 to time point t.

Hence, unlike the conventional nanopore sensing, where the event frequency is used as a parameter in the dose-response curve, the number of events (i.e., event counts) was used instead in this reaction time effect study. One advantage of replacing the event frequency with the number of events in the data analysis is that this approach can remedy the small event frequency issue, which is due to the low concentration of the degradation products at the early stage of an enzymatic reaction (especially for a reaction at a low concentration of protease), so that a long recording time is needed to collect enough events for the statistical analysis.

Figure 5:
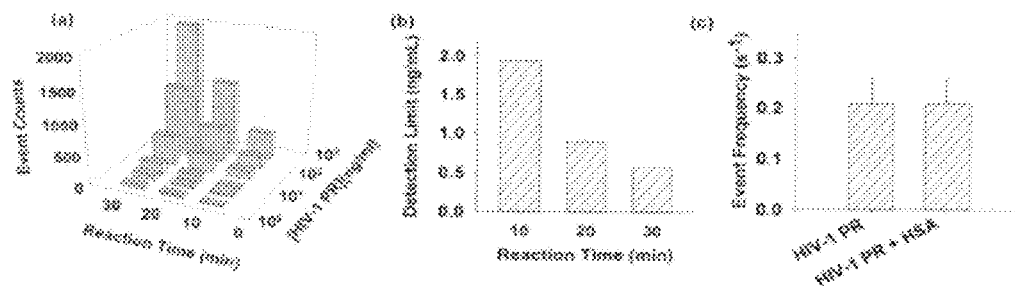
FIG. 5(a)-5(c) show characteristics of a HIV-1 protease nanopore sensor according to one embodiment of this invention.

FIG. 5 summarizes experimental results showing that, although the detection limit became worse with a decrease in the recording time, sensitive detection of HIV-1 protease was still able to be achieved even in a 10 minute recording with a detection limit as low as 1.93 ng/mL (equivalent to 193 pM). FIG. 5a is a dose-response curve for HIV-1 protease detection at various reaction times. FIG. 5b shows the effect of proteolytic reaction time on the detection limit. FIG. 5c summarizes an interference study for the HIV-1 protease nanopore detection system. The experiments were performed at −40 mV in 1 M NaCl solution buffered with 1 mM EDTA and 1 mM $NaH_2PO_4$ (pH 4.7) in the presence of 5 µM peptide FFSQNYPIVQ. The event counts in FIG. 5a were obtained after deducting the background signals. The concentrations of HIV-1 protease and HSA used in FIG. 5c were 30 ng/mL and 20 µM, respectively. The event frequency in FIG. 5c was calculated based on the total number of peptide events having mean residual currents of −9.5 pA collected in a 10 min single-channel recording.

Figure 6:
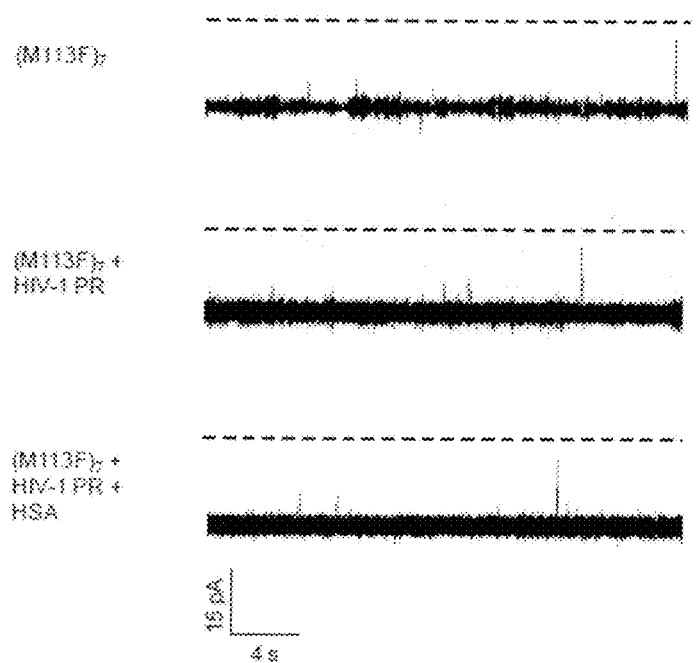
FIG. 6 shows representative single-channel recording trace segments of a mutant αHL protein $(M113F)_7$ pore with the HIV-1 protease and HSA protein.

To demonstrate the application of the nanopore sensor in the analysis of samples resembling those relevant for clinical analysis, two samples were examined. One sample contained only HIV-1 protease, while the other contained a mixture of human serum album (HSA) and HIV-1 protease (note that HSA is a dominant protein in human blood). Similar to the HIV-1 protease, due to its larger molecular size (with approximate dimensions of 80×80×30 Å) than the trans opening of the αHL protein pore (~20 Å), HSA cannot enter the nanopore and hence cannot produce current blockage events (FIG. 6). As a result, the event frequencies of these two protease samples were not significantly different (FIG. 5c), suggesting the developed nanopore sensor could effectively detect HIV-1 protease in the presence of other matrix components such as HSA. In summary, by direct monitoring of the events produced by the translocation of the substrate degradation products through a nanopore, a real-time, label-free method for the measurement of the activity of HIV-1 protease is provided.

Trypsin Sensor

A new type of biosensor was developed to measure the activity of trypsin based on the enzymatic reactions between β-amyloid (10-20) and trypsin in an α-hemolysin nanopore. Given its advantages of real time, label-free and low-cost analysis, the developed nanopore sensor design strategy should find useful applications in the development of stochastic sensors for other proteases of medical, pharmaceutical, and biological importance.

Trypsin is a serine protease with 223 amino acid residues (M.W.=23.8 kDa), which is the most important digestive enzyme produced in the pancreas as the inactive proenzyme trypsinogen. Trypsin cleaves peptide chains mainly at the carboxyl side of the amino acids lysine or arginine. Pancreatic trypsin production can be adversely affected by pathologies (e.g., pancreatitis), resulting in organ damage and release of enzyme into the blood. It is well known that the trypsin level is increased with some types of pancreatic diseases. Therefore, rapid and sensitive methods for trypsin detection, activity assay, and inhibitor screening are highly desired for the efficient diagnosis and treatment of pancreatic diseases.

Figure 8:
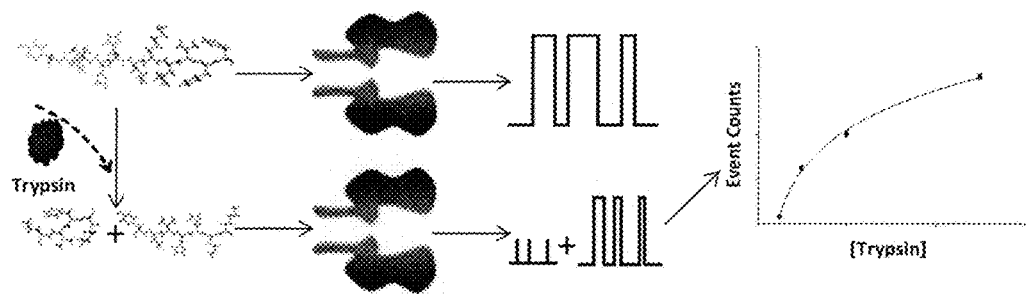
FIG. 8 is a schematic representation of the principle of nanopore detection of trypsin according to one embodiment of this invention.

The principle for nanopore detection of trypsin is shown in FIG. 8. When there is no presence of trypsin, the substrate peptide molecules could pass through the nanopore giving one signal reading, i.e., a type of characteristic current modulation events with unique residence time and blockage amplitude. By contrast, if trypsin is present in the solution, acting like scissors, it cuts the peptide molecules. The cleavage products produce entirely different current modulations from those of the substrate. A comparison of these events quantifies the trypsin concentration and enzymatic activity.

β-amyloid (10-20) peptide, the trypsin substrate, with a sequence of YEVHHQKLVFF was obtained from American Peptide Company (Sunnyvale, Calif.), while peptides YEVHHQK and LVFF (i.e., two substrate degradation fragments) were obtained from Biomatik Corporation (Wilmington, Del.). All the other chemicals were bought from Sigma-Aldrich (St. Louis, Mo.). Trypsin, peptides, and all the other chemicals were dissolved in HPLC-grade water (ChromAR, Mallinchkrodt Baker). Stock solutions of the peptides were prepared at 0.5 mM each, while that of trypsin was 100 µg/ml. All these solutions were kept at −20° C. before and after use. The electrolyte used contained 1.0 M NaCl buffered with 1 mM Tris, with the pH adjusted to 7.5 using HCl. Lipid 1,2-diphytanoylphosphatidylcholine was obtained from Avanti Polar Lipids (Alabaster, Ala.). Teflon film (25 µm thick) was purchased from Goodfellow (Malvern, Pa.).

Engineered α-hemolysin (αHL) (M113F)$_7$ protein nanopores were produced as mentioned above. Briefly, the mutant αHL M113F gene was constructed by site-directed mutagenesis (Mutagenex, Piscataway, N.J.) with a wild-type αHL gene in a T7 vector (pT7-αHL). The mutant αHL monomers were first synthesized by coupled in vitro transcription and translation using the E. coli T7 S30 Extract System for Circular DNA from Promega (Madison, Wis.). Subsequently, they were assembled into homoheptamers by adding rabbit red cell membranes and incubating for 1-2 hours. The heptamers were then purified by SDS-polyacrylamide gel electrophoresis and stored in aliquots at −80° C.

A bilayer of 1,2-diphytanoylphosphatidylcholine was formed on an aperture (150 µm) in a Teflon septum that divided a planar bilayer chamber into cis and trans compartments using the method of M. Montal and P. Mueller, Proc. Nat. Acad. Sci., 1972, 69, 3561-3566. Unless otherwise noted, all the experiments were performed under a series of symmetrical buffer conditions with a 1 M NaCl and 10 mM Tris (pH 7.5) at 24±1° C. The αHL protein was added to the cis compartment, which was connected to "ground", while the peptide substrate and trypsin were added to the trans compartment. The final concentration of the αHL proteins used for the single channel insertion was 0.2-2.0 ng/ml. Currents were recorded with a patch clamp amplifier (Axopatch 200B, Molecular Devices; Sunnyvale, Calif., USA). Currents were low-pass filtered with a built-in four-pole Bessel filter at 5 KHz and sampled at 50 KHz by a computer equipped with a Digidata 1440A converter (Molecular Devices).

Data were analyzed with the following software: pClamp 10.3 (Molecular Devices), Origin 8.0 (Microcal, Northampton, Mass.), and SigmaPlot 12.0 (Systat Software Inc., San Jose, Calif.). Conductance values were obtained from the amplitude histograms after the peaks were fit to Gaussian functions. Values of inter-event interval ($\tau_{on}$) and residence time ($T_{off}$) for the peptide events were obtained from the open state (1) and close state (0) dwell time histograms, respectively by fitting the distributions to single exponential functions by the Levenberg-Marquardt procedure. At least three separate experiments were carried out for each sample.

Figure 9:
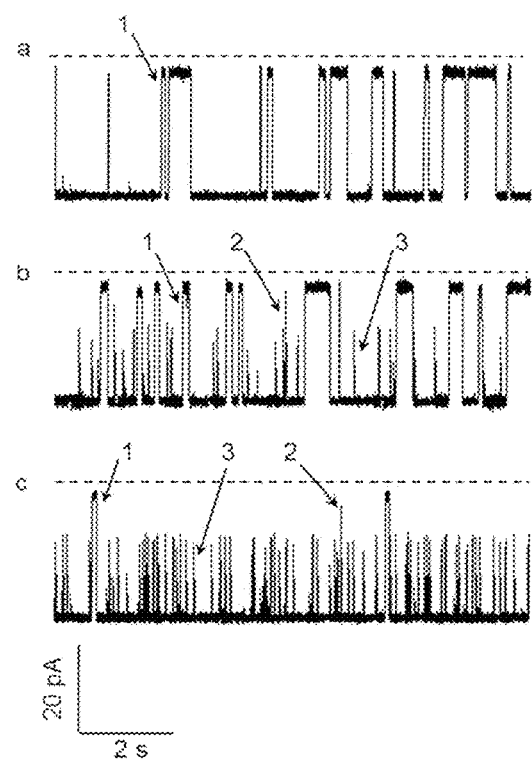
FIG. 9 shows typical single-channel recording trace segments after 30-min proteolytic cleavage of peptide β-amyloid (10-20) by trypsin at various concentrations: (a) 0 ng/ml; (b) 20 ng/ml; and (c) 100 ng/ml.

Initial experiments were carried out at an applied potential bias of −40 mV in 1 M NaCl solution buffered with 10 mM Tris (pH 7.5). The mutant αHL (M113F)$_7$ protein nanopore was used as the stochastic sensing element, while β-amyloid (10-20) peptide (sequence: YEVHHQKLVFF, 5 µM) was employed as the substrate. It is well known that trypsin cuts peptide bonds after arginine or lysine amino acid residues, while the αHL (M113F)$_7$ protein pore has been shown to offer an improved sensor resolution/sensitivity (e.g., prolonged event residence time for the analytes) over the wild-type αHL pore. Specifically, at this applied potential bias, all the three event parameters (i.e., residence time, frequency, and amplitude) for peptide translocation in the αHL nanopore had relatively large values; further, the open αHL channel was quiet without transient background current modulations. The experimental results are summarized in FIG. 9. In FIG. 9, dashed lines represent the levels of zero current. Label 1 shows the representative events attributed to the substrate, while labels 2 and 3 represent the events due to the cleavage products.

The experiments were performed at −40 mV in 1 M NaCl solution buffered with 10 mM Tris (pH 7.5) using the mutant α-hemolysin protein (M113F)$_7$ pore. The concentration of the substrate β-amyloid (10-20) was 5 µM. It is apparent that, with the β-amyloid (10-20) peptide alone in the solution, only one type of events was observed. These events had a mean residence time of ~0.31 s and a mean residual current of approximately −2.25 pA. In contrast, after addition of trypsin to the substrate-containing solution, two types of new events with much smaller residence times and amplitudes appeared. These two types of new events had similar residence time (~1.1 ms), but presented significantly different residual currents (~5 pA vs.~−12 pA), allowing them to be well separated and differentiated. Furthermore, the experiments showed that the frequencies of these two types of events increased with the recording time and with the increased concentration of added trypsin, a clear indication that they were attributed to the products formed by the trypsin's cleavage of the β-amyloid (10-20) peptide, i.e., YEVHHQK and LVFF, respectively. This result not only agreed very well with the fact that the spherical molecular diameter (38 Å) of trypsin is larger than that (20 Å) of the αHL transmembrane domain so that it cannot enter the pore, but also suggest that trypsin would not be denatured and pulled through the nanopore under the experimental condition, i.e., at a small applied voltage bias of −40 mV.

Under the same current experimental conditions (i.e., α-hemolysin (M113F)$_7$ pore, pH 7.5, −40 mV applied voltage bias), a series of experiments was carried out to investigate the proteolytic cleavage of the substrate peptide β-amyloid (10-20) by trypsin, with the concentration of the substrate constant (5 µM), but varied the trypsin concentration (ranging from 5 to 50 ng/mL). Similar to the observation described above, in addition to the substrate events, two new types of current modulations were identified in all of the different trypsin concentration situations, providing further evidence that these events were attributed to the substrate degradation products. It should be noted that, in principle, the two substrate cleavage products should have identical concentrations. However, due to the length and structure difference in these two peptide fragments, the event frequencies for their translocation in the nanopore might vary greatly. Since the LVFF events were significantly more frequent than the YEVHHQK events, for convenience, only LVFF events were included in the data analysis. It should be noted that, one advantage of obtaining enzyme kinetic information based on the substrate degradation product signal instead of the substrate signal as used in various conventional enzyme assays is that this new strategy permits the target protease to be differentiated from other potential interfering proteases if they cleave the peptide substrate at different positions, and hence improved sensor selectivity and accuracy could be accomplished. Furthermore, in a proteolytic reaction, the instantaneous concentrations and hence the event frequencies of the degradation products vary with the reaction time until all the substrate is degraded. Therefore, unlike conventional nanopore sensing, where the event frequency is used as a parameter in the dose-response curve, the number of event occurrences (i.e., event counts) was used in this investigation instead. One advantage of utilizing event counts instead of the event frequency in the data analysis is that this approach can significantly shorten the experimental recording time. Due to the low concentration of the degradation products at the early stage of an enzymatic reaction (especially for a reaction with a low concentration of protease), a long recording time is required to collect enough events for statistical analysis of the event frequency.

Figure 10:
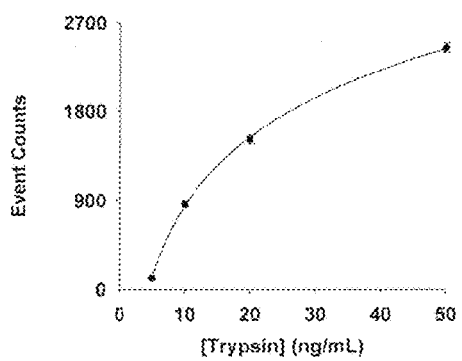
FIG. 10 is a dose-response curve for trypsin detection according to one embodiment of this invention.

FIG. 10 shows the plot of the number of LVFF events collected in a 30-min recording versus the trypsin concentration. It was found that the detection limit for trypsin (defined as the concentration corresponding to three times the standard deviation of a blank signal) in a 30-minute reaction period was 4.99 ng/mL (corresponding to 210 pM). Such a detection limit is more than sufficient for analysis of clinical samples (note that the trypsin concentration in healthy people's serum ranges from 140-400 ng/mL).

Figure 11:
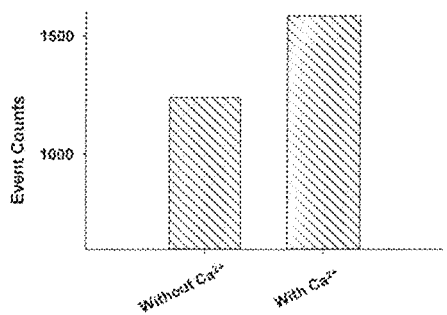
FIG. 11 summarizes the effect of $Ca^{2+}$ on the trypsin sensor sensitivity.

The existence of $Ca^{2+}$ ions in the solution can benefit the process of proteolytic reaction catalyzed by trypsin. Trypsin itself is a protein, and is capable of digesting itself. However, this autolysis process (more commonly known as self-digestion) can be prevented by $Ca^{2+}$ ions (due to their binding to trypsin). In addition, $Ca^{2+}$ ions can also promote the formation of active trypsin from trypsinogen, the protein produced in its inactive form within the pancreas of humans. To examine whether the existence of $Ca^{2+}$ ions in the electrolyte solution could improve the nanopore sensor sensitivity for trypsin analysis, the effect of $Ca^{2+}$ ions on the trypsin cleavage of the β-amyloid (10-20) peptide was further investigated. Experimental results, summarized in FIG. 11, showed that, compared with the electrolyte solution without $Ca^{2+}$, the buffer solution containing additional 5 mM $Ca^{2+}$ ions would result in a 28% increase in the number of LVFF events, confirming that $Ca^{2+}$ enhanced the sensor sensitivity.

Figure 12:
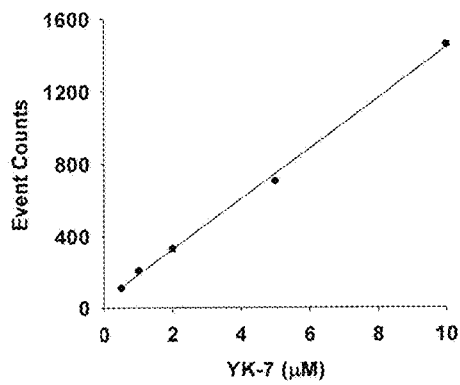
FIG. 12 is a dose response curve for the example peptide YEVHHQK.
Figure 13:
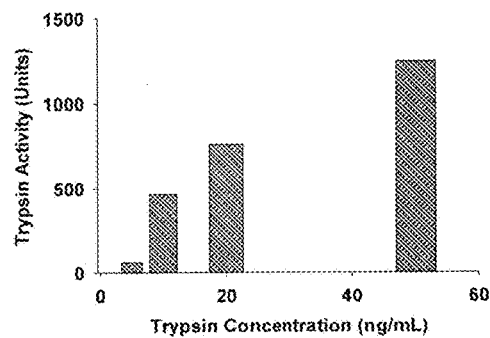
FIG. 13 is a plot of trypsin activity vs. concentration according to one embodiment of this invention.

Numerous methods have been utilized to study trypsin activity, including gel electrophoresis, gelatin-based film techniques, colorimetry, chemiluminescence, fluorescence, and electrochemical methods. Obviously, if more frequent events are observed for the substrate cleavage products, a stronger protease activity could be expected. In order to measure the activity of trypsin by nanopore analysis, a modified version of the universal protease activity assay was developed. Briefly, peptide YEVHHQK, one of the cleavage products of the substrate β-amyloid (10-20) peptide, was custom synthesized, and the dose-response curve (event counts vs. peptide concentration), shown in FIG. 12, for its translocation in the nanopore was constructed. By comparing the number of events of YEVHHQK generated by the trypsin cleavage of β-amyloid (10-20) with this calibration curve, the concentration of YEVHHQK in the enzymatic reaction mixture solution could be obtained. Then, the activity of trypsin could be determined in terms of Units, which is the amount of micromoles of the peptide YEVHHQK fragment released from the substrate per minute. The activities of trypsin at various concentrations were summarized in FIG. 13.

Figure 14:
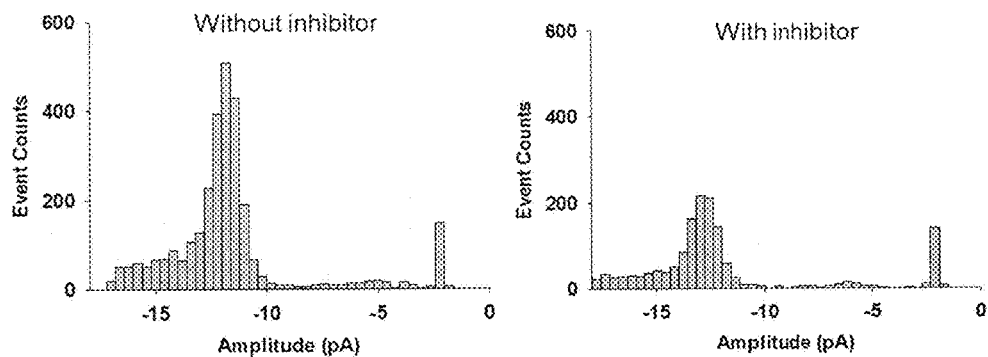
FIG. 14 summarizes the effect of inhibitor on trypsin digestion of β-amyloid (10-20) according to one embodiment of this invention.

To demonstrate the feasibility of utilizing the nanopore sensing platform of this invention as a screening tool for protease inhibitors, trypsin cleavage of the β-amyloid (10-20) peptide was further investigated in the presence of the trypsin inhibitor from bovine pancreas (TIBP), a small globular protein with 58 amino acid residues (M.W.=6.5 kDa). In principle, TIBP would bind to trypsin, thus inhibiting trypsin cleavage of β-amyloid (10-20) peptide. Therefore, compared with the situation without trypsin inhibitor, the presence of TIBP in the solution would lead to a decrease in the event frequency of the substrate cleavage products. FIG. 14 summarizes experiments that showed, in the absence of TIBP, 2075 LVFF events were observed in a 456-s single-channel recording. In contrast, in the presence of TIBP, the number of LVFF events in the same time frame decreased to 1030. The results confirmed that TIBP could indeed inhibit trypsin activity.

Thus the biosensor of this invention measured the activity of trypsin by monitoring the enzymatic reactions between the substrate and trypsin in an α-hemolysin nanopore. Given its advantages of real time, label-free and low-cost analysis, the nanopore sensing strategy should find useful applications in the development of stochastic sensors for other proteases of medical, pharmaceutical, and biological importance.

Nucleic Acid Sensor

A label-free real-time nanopore sensing method and system for the detection of anthrax lethal factor, a component of the anthrax toxin, was prepared and tested by using a complementary single-stranded DNA as a molecular probe.

DNA samples of standard purification (desalting) were purchased from Intergrated DNA Technologies (Coralville, Iowa). All the other chemicals were ordered from Sigma-Aldrich (St. Louis, Mo.). All of the DNA samples and chemicals were dissolved in HPLC-grade water (ChromAR, Mallinckrodt Baker). All the stock solutions of DNA polymers were prepared at 5 mM each, and kept at −20° C. before and after use. Three electrolyte solutions were used in this work, which contained 0.15/1.0/3.0 M NaCl buffered with 10 mM Trizma base, with the pH adjusted to 7.5 using hydrochloride acid. Lipid 1,2-diphytanoylphosphatidylcholine was obtained from Avanti Polar Lipids (Alabaster, Ala.). Teflon film (25 um thick) was purchased from Goodfellow (Malvern, Pa.).

The mutant αHL M113F gene was constructed by site-directed mutagenesis (Mutagenex, Piscataway, N.J.) with a wild-type αHL gene in a T7 vector (pT7-αHL). The mutant αHL monomers were first synthesized by coupled in vitro transcription and translation (IVTT) using the E. Coli T7 S30 Extract System for Circular DNA from Promega (Madison, Wis.). Subsequently, they were assembled into homoheptamers by adding rabbit red cell membranes and incubating for 1-2 hours. The heptamers were then purified by SDS-polyacrylamide gel electrophoresis and stored in aliquots at −80° C.

A bilayer of 1,2-diphytanoylphosphatidylcholine was formed on an aperture (150 μm) in a Teflon septum that divided a planar bilayer chamber into cis and trans compartments. The formation of bilayer was achieved using the Montal et al. method discussed above. Unless otherwise noted, all the experiments were performed under symmetrical buffer conditions with a 2.0 mL solution comprising 1 M NaCl, and 10 mM Tris.HCl (pH 7.5) at 26±1° C. Both the αHL protein and the DNA polymers were added to the cis compartment, which was connected to "ground". The final concentration of the αHL proteins used for the single channel insertion was 0.2-2.0 ng·mL$^{-1}$. The transmembrane potential, which was applied with Ag/AgCl electrodes with 3% agarose bridges containing 3 M KCl, was +180 mV, unless otherwise noted. A positive potential indicates a higher potential in the trans chamber of the apparatus. Currents were recorded with a patch clamp amplifier (Axopatch 200B, Molecular Devices; Sunnyvale, Calif., USA). They were low-pass filtered with a built-in four-pole Bessel filter at 5 KHz and sampled at 50 KHz by a computer equipped with a Digidata 1322A/D converter (Molecular Devices).

Data were analyzed with the following software: pClamp 10.3 (Molecular Devices), Origin 8.0 (Microcal, Northampton, Mass.), and SigmaPlot 12.0 (Systat Software Inc., San Jose, Calif.). Conductance values were obtained from the amplitude histograms after the peaks were fit to Gaussian functions. The values of $\tau_{on}$ (the mean interevent interval) and $\tau_{off}$ (the mean residence time) for DNA polymers were obtained from the dwell time histograms by fitting the distributions to single exponential functions by the Levenberg-Marquardt procedure. Thermodynamics of hairpin folding and DNA hybridization was obtained from the DINAMelt web server.

As shown in FIG. 15, in the absence of the target pathogen gene segment, the translocation of the cDNA probe through the nanopore produces only one major type of current modulation events. In contrast, in the presence of the target DNA sequence, two complementary DNA monomers will be hybridized in the solution to form dsDNA molecules. Due to their larger molecular sizes than those of ssDNA molecules, the interaction between the dsDNA and the nanopore may result in a new type of current modulation events having different signatures from those of the cDNA probe and the single stranded pathogen gene segment, e.g., with longer residence times and/or showing complicated sub-state current modulation features.

Figure 20:
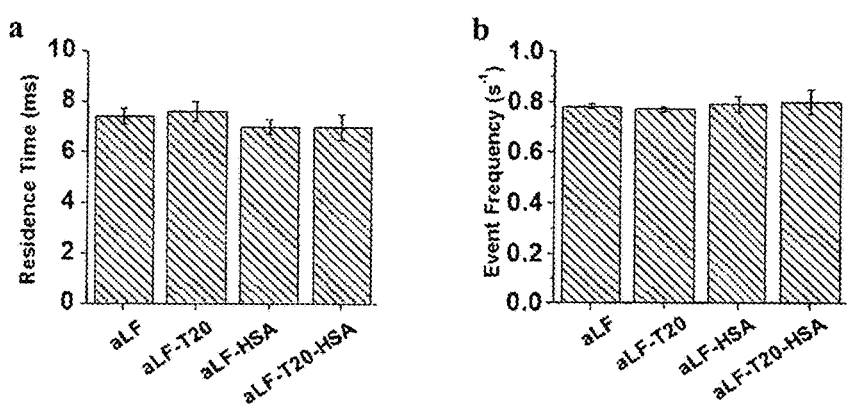
FIG. 20 summarizes the effect of matrix components on the (a) mean residence time and (b) frequency of the aLF-cDNA probe duplex events.

To demonstrate this concept, a characteristic 20-base gene segment (SEQ ID NO:1: 5'-GGATTATTGTTAAATATTGA-3') of anthrax lethal factor (aLF), a component of the anthrax toxin, was employed as the target pathogen molecule, while an engineered version of the αHL protein, $(M113F)_7$, was used as the nanopore sensing element. The initial experiments were carried out at an applied potential bias of +120 mV and using a 20-base ssDNA (SEQ ID NO:2: 5'-TCAATATTTAACAATAATCC-3') as the molecular probe, which can form blunt-ended double-stranded DNA with the target analyte. The experimental results, summarized in FIG. 16, showed that, without the target aLF DNA sample, the single-stranded cDNA probe produced only one major type of current modulation events in the nanopore, with a mean residence time of 0.20±0.01 ms. However, upon addition of the target aLF DNA molecules to the cDNA probe-containing solution, a new type of events with a mean residence time of 620±63 ms was observed.

As the aLF sample alone also only produced short-lived events with a mean residence time of 0.31±0.01 ms, the three-order increase in the event residence time suggests that the cDNA probe and the target aLF indeed formed DNA duplexes. According to the theoretical prediction (using the DINAMelt web server), both the probe and target DNA molecules could form thermodynamically stable hairpin loop structures (the $T_m$ values were 30.9° C. and 34.9° C., respectively). The event residence times of these DNA hairpins were not significantly different from those of the well-studied ssDNA molecules with the same length; so the experimental results suggest that the closed states of these hairpin loop structures could be rapidly unfolded and driven through the nano-channel under our experimental conditions. As the target aLF DNA has a slightly larger folding free energy (ΔG=−0.72 kcal/mol vs. −0.42 kcal/mol), and hence more stable than the cDNA probe, it is not unreasonable that the aLF sample is more difficult to be unfolded, thus producing events with a longer mean residence time than the cDNA probe (0.31 ms vs. 0.20 ms). In contrast, when both the cDNA probe and the target aLF monomers are present in the solution, they would be able to form a very stable fully-matched DNA duplex with ΔG of −12.2 kcal/mol. Hence, significantly longer residence time events were observed.

These long-lived dsDNA events also exhibited sub-state current modulations, a clear indication that they might be attributed to the unzipping and translocation of the DNA duplex through the αHL channel. This interpretation was further supported by the voltage dependence study, where the mean residence time of the long-lived events decreased as the applied potential bias increased (FIG. 17). More interestingly, it was noticed that these sub-state current modulation events showed two different intermediate levels, level 1 and level 2 as shown in FIG. 16. One likely reason is that these events were attributed to the two different orientations in which the dsDNA entered the nanopore. According to DINAMelt, in a mixture of equal amounts of the cDNA probe and the target aLF molecules, the cDNA-aLF hybrid duplexes (with one end containing a GC base pair and the other having a AT base pair) are the dominant species (>99.9%), while other DNA species or structures such as homodimers and hairpins could be neglected.

To study the aLF sensor selectivity, two other DNA samples, aLF-1 and aLF-2, were examined at +120 mV. These two samples had sequences of 5'-GGATTATTGTGAAATATTGA-3' (SEQ ID NO:3), and 5'-GGATTATGGTGAAATATTGA-3' (SEQ ID NO:4), respectively, which were different from the target analyte aLF (SEQ ID NO:4: 5'-GGATTATTGTTAAATATTGA-3') only by a single base, and two bases (note that the mismatch portion are highlighted). The experimental results showed that the event mean residence times of the aLF-1 and aLF-2 samples were 342±35 ms and 57.4±2.5 ms, respectively. These values were about two-folds and ten-folds smaller than the residence time of the target aLF sample. The results are not unreasonable considering that the aLF-1/aLF-2 and the cDNA probe are able to form double-stranded DNA having single base-pair/two base-pair mismatches, which are less stable than the fully-matched aLF-cDNA duplexes, thus needing less time to be unzipped by the nanopore. This interpretation is supported by the predicted theoretical hybridization free energy between these DNA samples and the cDNA probe (using the DINAMelt web server), which were −12.2 kcal/mol, −10.9 kcal/mol, and −9.6 kcal/mol for aLF, aLF-1, and aLF-2, respectively. As added multiple-base mismatch controls, two additional DNA polymers $A_{20}$ (SEQ ID NO:5: AAAAAAAAAAAAAAAAAAAA) and $T_{20}$ (SEQ ID NO:6: TTTTTTTTTTTTTTTTTTTT) were also examined. Their event residence times were 11.7±0.2 and 0.12±0.01 ms, respectively, which was in agreement with our observation that with an increase in the number of the base-pair mismatches of the dsDNA sample, the DNA duplex became less stable, leading to a decrease in the event mean residence time (FIG. 18).

To validate applicability of the nanopore sensor to samples resembling those relevant for clinical analysis, two samples were initially examined with the $(M113F)_7$ protein pore in the presence of the cDNA probe and under the symmetric electrolyte condition. One sample contained human serum album (HSA), while the other contained a mixture of aLF and HSA (note that HSA is the dominant protein in human blood). As shown in FIG. 19, without aLF, the HSA sample only produced short-lived events with a mean residence time of 0.04 ms. Since in the absence of the cDNA probe, HSA alone didn't produce any current modulations, it is apparent that these rapid events were attributed to the cDNA probe. In sharp contrast, the mixture sample produced significantly longer duration events with a mean residence time of 7.5 ms, which was similar to that of the single aLF standard. Furthermore, the frequency of the long-lived events of the aLF-cDNA probe duplexes didn't change significantly in the absence/presence of HSA. To demonstrate the feasibility of the developed nanopore sensor in the analysis of aLF in the presence of other DNA molecules or in more complicated mixtures, two additional samples were examined: one contained a mixture of aLF and T20, while the other was consisted of aLF, T20, and HSA. The experimental results, summarized in FIG. 20 showed that both the residence time and the frequency of the long-lived events for the mixture samples were similar to those of aLF alone. Taken together, the combined results suggest that our developed nanopore sensor can effectively detect aLF in the presence of other matrix components.

In summary, a rapid and sensitive nanopore sensing method for the label-free real-time detection of anthrax lethal factor was developed. By using an unmodified complementary single-stranded DNA as a molecular probe, and monitoring the hybridization interaction between a target single-stranded aLF gene segment and the cDNA probe, picomolar concentrations of aLF DNA could be detected in approximately 1 minute. Further, the method is selective, and other ssDNA molecules including those differing by only a single base will not interfere with the detection of the target aLF DNA. This sequence-specific detection approach should find useful application in the development of nanopore sensors for the detection of other pathogens.

The invention thus provides a real time, label-free and low-cost biomarker analysis nanopore sensor design useful in applications in the development of stochastic sensors for medical, pharmaceutical, and biological importance. Given the high sensitivity of the method and its potential to discriminate the target biomarker from false positives, the nanopore sensor design strategy can be used for stochastic sensors for various biomarker, especially those have potential clinical values for disease diagnosis or prognosis, and have become priority targets for new pharmaceuticals.

The invention illustratively disclosed herein suitably may be practiced in the absence of any element, part, step, component, or ingredient which is not specifically disclosed herein.

While in the foregoing detailed description this invention has been described in relation to certain preferred embodiments thereof, and many details have been set forth for purposes of illustration, it will be apparent to those skilled in the art that the invention is susceptible to additional embodiments and that certain of the details described herein can be varied considerably without departing from the basic principles of the invention.

What is claimed is:

1. A system for sensing or characterizing a proteolytic enzyme, said system comprising a nanopore sensor to determine a current modulation of a sample including a polypeptide substrate, and a predetermined substrate current modulation signature for comparison to a current signature from the nanopore sensor.

2. The system of claim 1, wherein the nanopore sensor comprises:
   a first fluid compartment and a second compartment;
   a membrane separating the first fluid compartment and the second fluid compartment;
   a nanopore through the membrane that fluidically connects the first fluid compartment and the second fluid compartment;
   a power supply in electrical contact with said membrane to provide an electric potential difference between the first fluid compartment and the second fluid compartment; and
   a detector to detect an electrical current through the nanopore as the polypeptide substrate or components thereof, transits the nanopore under an applied electric potential difference between the first and second fluid compartments.

3. The system of claim 1, wherein the polypeptide substrate comprises more than one cleavage site each cleaved by one of two different proteolytic enzymes.

4. The system of claim 3, wherein the predetermined substrate current modulation signature corresponds to cleavage products resulting from both of the two different proteolytic enzymes.

5. The system of claim 3, wherein the predetermined substrate current modulation signature comprises a current modulation signature corresponding to the presence of cleavage products of the two different proteolytic enzymes.

6. The system of claim 1, further comprising a modified polypeptide substrate for a target proteolytic enzyme.

7. The system of claim 6, wherein the modified polypeptide substrate provides cleavage segments of different lengths upon contact with the target proteolytic enzyme.

8. The system of claim 6, wherein the polypeptide substrate has been modified to include at least one additional amino acid.

9. A system for sensing or characterizing a proteolytic enzyme, said system comprising:
   a first fluid compartment and a second fluid compartment;
   a membrane separating the first fluid compartment and the second fluid compartment;
   a nanopore through the membrane that fluidically connects the first fluid compartment and the second fluid compartment, wherein the nanopore sensor is adapted to determine a current modulation of a sample including a polypeptide substrate;
   a power supply in electrical contact with said membrane to provide an electric potential difference between the first fluid compartment and the second fluid compartment; and
   a detector to detect an electrical current through the nanopore as the polypeptide substrate or a component thereof, transits the nanopore under an applied electric potential difference between the first and second fluid compartments; and
   a predetermined substrate current modulation signature of the polypeptide substrate or at least one component thereof for comparison to a current signature from the nanopore sensor, wherein a presence of the proteolytic enzyme in the sample is determined by comparing the current signature to the predetermined substrate current modulation signature.

10. The system of claim 9, wherein the predetermined substrate current modulation signature corresponds to a cleavage product resulting from the proteolytic enzyme.

11. The system of claim 10, wherein a difference between the current signature and the predetermined substrate current modulation signature indicates the presence of the proteolytic enzyme.

12. The system of claim 10, wherein the polypeptide substrate comprises more than one cleavage site each cleaved by one of two different proteolytic enzymes.

13. The system of claim 9, further comprising an amount of the polypeptide substrate.

14. The system of claim 13, wherein the amount of the polypeptide substrate comprises a modified polypeptide substrate having cleavage segments of different lengths.

15. The system of claim 9, wherein the proteolytic enzyme is selected from a retroviral aspartyl protease, a metalloprotease, a serine protease, a cysteine protease, a threonine protease, or an aspartic protease.

16. A method for sensing or characterizing a biomarker using the system of claim 2, the method comprising:
   introducing a sample to the first fluid compartment;
   applying an electric field across said membrane;
   monitoring a sample current modulation signature across the membrane; and
   determining a presence of the biomarker in the sample as a function of the sample current modulation signature.

* * * * *

SEQUENCE LISTING

```
<160> NUMBER OF SEQ ID NOS: 6

<210> SEQ ID NO 1
<211> LENGTH: 20
<212> TYPE: DNA
<213> ORGANISM: Bacillus anthracis

<400> SEQUENCE: 1
ggattattgt taaatattga                                                  20

<210> SEQ ID NO 2
<211> LENGTH: 20
<212> TYPE: DNA
<213> ORGANISM: Bacillus anthracis

<400> SEQUENCE: 2
tcaatattta acaataatcc                                                  20

<210> SEQ ID NO 3
<211> LENGTH: 20
<212> TYPE: DNA
<213> ORGANISM: Bacillus anthracis

<400> SEQUENCE: 3
ggattattgt gaaatattga                                                  20

<210> SEQ ID NO 4
<211> LENGTH: 20
<212> TYPE: DNA
<213> ORGANISM: Bacillus anthracis

<400> SEQUENCE: 4
ggattatggt gaaatattga                                                  20

<210> SEQ ID NO 5
<211> LENGTH: 20
<212> TYPE: DNA
<213> ORGANISM: Artificial Sequence
<220> FEATURE:
```

-continued

```
<223> OTHER INFORMATION: The sequence is synthesized

<400> SEQUENCE: 5
aaaaaaaaaa aaaaaaaaaa                                              20

<210> SEQ ID NO 6
<211> LENGTH: 20
<212> TYPE: DNA
<213> ORGANISM: Artificial Sequence
<220> FEATURE:
<223> OTHER INFORMATION: The sequence is synthesized

<400> SEQUENCE: 6
tttttttttt tttttttttt                                              20
```